US010123977B2

(12) United States Patent
Tsurushima et al.

(10) Patent No.: US 10,123,977 B2
(45) Date of Patent: Nov. 13, 2018

(54) GEL PATCH

(71) Applicant: HISAMITSU PHARMACEUTICAL CO., INC., Tosu-shi, Saga (JP)

(72) Inventors: Keiichiro Tsurushima, Tosu (JP); Yasuhisa Kose, Tosu (JP); Takaaki Yoshinaga, Tosu (JP)

(73) Assignee: HISAMITSU PHARMACEUTICAL CO., INC., Tosu-Shi, Saga (JP)

( * ) Notice: Subject to any disclaimer, the term of this patent is extended or adjusted under 35 U.S.C. 154(b) by 0 days.

(21) Appl. No.: 14/974,288

(22) Filed: Dec. 18, 2015

(65) Prior Publication Data
US 2016/0175262 A1 Jun. 23, 2016

(30) Foreign Application Priority Data

Dec. 22, 2014 (JP) .................................. 2014-258879
Sep. 10, 2015 (JP) .................................. 2015-178693

(51) Int. Cl.
*A61K 47/14* (2017.01)
*A61K 9/70* (2006.01)
*A61K 31/618* (2006.01)
*A61K 47/26* (2006.01)

(52) U.S. Cl.
CPC .......... *A61K 9/7061* (2013.01); *A61K 31/618* (2013.01); *A61K 47/14* (2013.01); *A61K 47/26* (2013.01)

(58) Field of Classification Search
None
See application file for complete search history.

(56) References Cited

U.S. PATENT DOCUMENTS

2007/0148216 A1 6/2007 Yoshitake et al.
2014/0302118 A1* 10/2014 Kawamura .......... A61K 9/7061
424/449

FOREIGN PATENT DOCUMENTS

| EP | 0452837 A2 | 10/1991 |
| JP | 0372416 A | 3/1991 |
| JP | H4-1127 A | 1/1992 |
| JP | H8-119859 A | 5/1996 |
| JP | 09208462 A | 8/1997 |
| JP | 2002-104954 A | 4/2002 |
| JP | 2003093434 A | 4/2003 |
| JP | 2004-67562 A | 3/2004 |
| JP | 2004-256396 A | 9/2004 |
| JP | 2005-239679 A | 9/2005 |
| JP | 2011-140501 A | 7/2011 |
| WO | 2005/023307 A1 | 3/2005 |
| WO | 2006090782 A1 | 8/2006 |
| WO | 2012102242 A1 | 8/2012 |
| WO | 2013012000 A1 | 1/2013 |
| WO | WO 2013027840 A1 * | 2/2013 ........... A61K 9/7061 |
| WO | 2015025935 A1 | 2/2015 |

OTHER PUBLICATIONS

Machine translation of WO 2012/102242, original document published Aug. 2012.*
Translation of tables in WO 2012/102242, original document published Aug. 2012.*
International Search Report dated Feb. 9, 2016 corresponding to International application No. PCT/JP2015/084971.
European Search report dated Mar. 17, 2017 in corresponding European Application No. 14837171.9.
International Preliminary Report on Patentability dated Jun. 27, 2017 issued in corresponding International Application No. PCT/JP2015/084971.
English translation of Written Opinion of the International Searching Authority dated Feb. 9, 2016 issued in corresponding in corresponding International Application No. PCT/JP2015/084971.
Office Action dated Dec. 1, 2017 issued in U.S. Appl. No. 15/536,994.

* cited by examiner

*Primary Examiner* — Nissa M Westerberg

(74) *Attorney, Agent, or Firm* — Nath, Goldberg & Meyer; Tanay E. Harkins

(57) ABSTRACT

A gel patch includes a base fabric, an adhesive layer, and a release liner in this order, wherein the adhesive layer contains a physiologically active substance, a water-soluble (meth)acrylic polymer, water, a surfactant, and poly(methyl acrylate/2-ethylhexyl acrylate), and the surfactant comprises a polyethylene glycol fatty acid ester or a polyoxyethylene sorbitan fatty acid ester.

5 Claims, No Drawings

GEL PATCH

CROSS REFERENCE TO RELATED APPLICATION

This application claims the benefits of Japanese Patent Application No. 2014-258879 filed Dec. 22, 2014, and 2015-178693 filed Sep. 10, 2015, the disclosures of which are incorporated by references herein in its entirety.

BACKGROUND

The present subject matter relates to a gel patch. Gel patches are a type of a poultice, which is provided with an adhesive layer containing drugs formed onto a base fabric, and the adhesive layer is usually coated with a release liner. For example, a gel patch with an expandable support is disclosed in JP2003-93434A. Since gel patches generally include a large amount of moisture and have a thick adhesive layer, the penetration of active components through the skin is promoted and stimulation on the skin is reduced. However, because the moisture in the adhesive layer is evaporated over time, the adhesion of the gel patch will degrade with time.

BRIEF SUMMARY

The instant subject matter is directed to gel patches comprising a base fabric, an adhesive layer, and a release liner in this order, wherein the adhesive layer contains a physiologically active substance, a water-soluble (meth)acrylic polymer, water, a surfactant, and poly(methyl acrylate/2-ethylhexyl acrylate). The surfactant can comprise a polyethylene glycol fatty acid ester or a polyoxyethylene sorbitan fatty acid ester.

DETAILED DESCRIPTION

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present teachings remain operable. Moreover, two or more steps or actions may be conducted simultaneously.

As described herein and has been newly found, if poly (methyl acrylate/2-ethylhexyl acrylate) is contained in an adhesive layer of a gel patch, degradation of adhesion can be suppressed, but the peeling strength (peeling force of the liner) at the time of peeling of the release liner from the adhesive layer may also become high.

In one embodiment, the present subject matter is a gel patch comprising a base fabric, an adhesive layer, and a release liner in this order, wherein the adhesive layer contains a physiologically active substance, a water-soluble (meth)acrylic polymer, water, a surfactant, and poly(methyl acrylate/2-ethylhexyl acrylate). The surfactant can include a polyethylene glycol fatty acid ester or a polyoxyethylene sorbitan fatty acid ester.

According to this gel patch, time degradation of adhesion can be prevented while easy peel of the liner is maintained. That is, high adhesive strength is maintained and the release liner can be peeled with less force.

In an embodiment, the poly(methyl acrylate/2-ethylhexyl acrylate) is derived from a poly(methyl acrylate/2-ethylhexyl acrylate) emulsion, and the surfactant includes a monofatty acid ester of polyethylene glycol (hereinafter may also be referred to as "PEG") or a monofatty acid ester of polyoxyethylene sorbitan. In another embodiment, the fatty acid constituting the monofatty acid ester is a fatty acid having 12 to 18 carbon atoms and such fatty acid having 12 to 18 carbon atoms includes stearic acid or oleic acid.

As used herein, the term "liner peel force" means the peeling strength for peeling a release liner from an adhesive layer of a gel patch (i.e., the load required for peeling).

The liner peel force is preferably 0.11 N/25 mm or less, more preferably 0.10 N/25 mm or less, considering the usefulness of the gel patch. When the liner peel force is 0.11 N/25 mm or less, the user thereof may find no difficulty in peeling the release liner.

An embodiment of the present subject matter is a gel patch provided with an adhesive layer formed on a base fabric, which further comprises a release liner arranged on a back side of a surface contacting the base fabric of the adhesive layer. In this embodiment, the adhesive layer contains a physiologically active substance, a water-soluble (meth)acrylic polymer, water, a surfactant, and poly(methyl acrylate/2-ethylhexyl acrylate). Further in this embodiment, the surfactant comprises a polyethylene glycol fatty acid ester or a polyoxyethylene sorbitan fatty acid ester. More specifically, in the gel patch of the present embodiment, the base fabric, the adhesive layer, and the release liner are laminated together in this order.

Examples of the base fabric include, but are not limited to, woven fabric, nonwoven fabric, a resin film, a foamed sheet, and paper, and examples of the woven fabric include, but are not limited to, knitted fabric. When woven fabric, nonwoven fabric, or a resin film is used as the base fabric, examples of a material thereof include, but are not limited to, polyolefins such as polyethylene, polypropylene, and polybutylene; polyesters such as polyethylene terephthalate; rayon; polyurethane; and cotton. One of these materials can be used alone or two or more of them can be used in combination. The base fabric may include a single layer structure or may include a multilayer structure. For the material of the base fabric, polyester is more preferable.

For the base fabric, nonwoven fabrics or woven fabrics are preferable, and nonwoven fabric or woven fabric having a predetermined elongation recovery rate is particularly preferable. The term "elongation recovery rate" herein refers to a value measured in compliance with "JIS L 1096 Testing Methods for Woven and Knitted Fabrics". It is preferable to use the nonwoven fabric or woven fabric having the predetermined elongation recovery rate because the base fabric expands in accordance with the motion of the portion in which the gel patch is applied onto movable portions such as a joint.

When the base fabric is nonwoven fabric, for example, the load applied when expanded by 50% is preferably 1 to 5 N/2.5 cm in the longitudinal direction (in the long axis direction) and 0.1 to 3 N/2.5 cm in the horizontal direction (in the short axis direction). The recovery rate at expansion by 50% is preferably 60 to 99%, for example, preferably 65 to 95%, and more preferably 70 to 90%. A suitable surface density is 80 to 120 g/m2, preferably 90 to 110 g/m2, for example. A suitable thickness of the base fabric is 0.5 to 2 mm, for example. The bending resistance of the base fabric (the measuring method for the bending resistance is the 45° cantilever method provided in JIS L 1096) can be 20 to 40 mm in the longitudinal direction (in the long axis direction) and 10 to 35 mm in the horizontal direction (in the short axis direction), and is preferably 25 to 35 mm in the longitudinal direction (in the long axis direction) and 15 to 30 mm in the horizontal direction (in the short axis direction).

When woven fabric, in particular, knitted fabric, is used as the base fabric, for example, the knitted fabric includes knitted fabric obtained by working the material into the form of a cloth by aggregating the stitches by circular knitting, warp knitting, weft knitting, or the like, for example. Preferable examples of the knitted fabric include, but are not limited to, a knitted fabric obtained by using one alone or two or more in combination of materials such as polyester-based material, nylon-based material, polypropylene-based material, rayon-based material. A knitted fabric including polyester-based polyethylene terephthalate which has a little interaction with a drug is particularly preferable.

In particular, when the base fabric is woven fabric, the load applied when expanded by 50% is preferably 1 to 5 N/2.5 cm in the longitudinal direction (in the long axis direction) and 0.1 to 3 N/2.5 cm in the horizontal direction (in the short axis direction), for example. The recovery rate at expansion by 50% is preferably 60 to 99%, for example, preferably 65 to 95%, and more preferably 70 to 90%. The bending resistance of the base fabric can be 10 to 30 mm in the longitudinal direction (in the long axis direction) and 10 to 30 mm in the horizontal direction (in the short axis direction), and is preferably 15 to 25 mm in the longitudinal direction (in the long axis direction) and 15 to 25 mm in the horizontal direction (in the short axis direction).

When a paste containing water is spread on a woven fabric, there is a threat of water seeping through the mesh of the woven fabric. However, if the surface density of the fabric made of polyethylene terephthalate is within 80 to 150 g/m², the paste tends to be securely spread without the water contained in the paste seeping through the mesh of the woven fabric, and also, thereby the anchoring property between the woven fabric and the paste can be maintained.

Preferably, the polyethylene terephthalate woven fabric has a modulus in the longitudinal direction (in the long axis direction) of 2 to 12 N/5 cm and a modulus in the horizontal direction (in the short axis direction) of 2 to 8 N/5 cm (the modulus as measured according to JIS L 1018:1999). When the modulus is lower than 2 N/5 cm (in the longitudinal direction) or 2 N/5 cm (in the horizontal direction), when the paste is applied, the woven fabric extends, and thus the adhesive may seep through the mesh and thereby the function as the gel patch may degrade. When the modulus is higher than 12 N/5 cm (in the longitudinal direction) or 8 N/5 cm (in the horizontal direction), the expansion property may become poor, and thus it may become difficult for the resulting gel patch to follow the expansion of the skin when the gel patch is applied to a bending portion.

In one embodiment, the adhesive layer contains a physiologically active substance, a water-soluble (meth)acrylic polymer, water, a surfactant, and poly(methyl acrylate/2-ethylhexyl acrylate), and the above-described surfactant comprises a polyethylene glycol fatty acid ester or a polyoxyethylene sorbitan fatty acid ester.

The physiologically active substance may be a substance having an endermic characteristic that exhibits its pharmacological activity when administered into a subject's body. The physiologically active substance may be a water-soluble substance or a fat-soluble substance. Because the adhesive layer of a gel patch contains a large quantity of water, the physiologically active substance is preferably a water-soluble substance. When the physiologically active substance is a fat-soluble substance, the physiologically active substance may be a substance that has an action of a surfactant. Examples of the physiologically active substance include, but are not limited to, non-steroid anti-inflammatory agents, or esters thereof, such as felbinac, flurbiprofen, diclofenac, diclofenac sodium, methyl salicylate, glycol salicylate, indomethacin, ketoprofen, and ibuprofen; antihistamine agents such as diphenhydramine and chlorpheniramine; pain killers such as aspirin, acetaminophen, ibuprofen, and loxoprofen sodium; local anesthetics such as lidocaine and dibucaine; muscle relaxants such as suxamethonium chloride; anti-fungal agents such as clotrimazole; anti-hypertensive agents such as clonidine; vasodilators such as nitroglycerine and isosorbide dinitrate; vitamin preparations such as vitamin A, vitamin E (tocopherol), tocopherol acetate, vitamin K, octotiamine, and riboflavin butyrate; prostaglandins; scopolamine; fentanyl; chile pepper extracts; and nonanoic acid vanillylamides. For the physiologically active substance, one type thereof may be used alone or two or more types of them can be used in combination.

In addition, the adhesive layer may contain fruit-derived components such as one or more of rose fruit extract, orange extract, orange fruit juice, raspberry extract, kiwi extract, cucumber extract, gardenia extract, grapefruit extract, hawthorn extract, Japanese pepper extract, quickthorn extract, juniper extract, jujubi extract, *Lansium domesticum* extract, tomato extract, grape extract, luffa extract, lime juice, apple extract, apple fruit juice, lemon extract, and lemon fruit juice; water-soluble placenta extract; allantoin; lecithin; amino acids; kojic acid; proteins; saccharides; hormones; placental extracts; ingredients extracted from various types of herbal medicines such as aloe and licorice; and extracts and substances such as *Angelica keiskei* extract, avocado extract, sweet hydrangea leaf extract, marshmallow extract, arnica extract, Ginkgo extract, aqua anisi extract, *Curcuma* extract, oolong tea extract, *Scutellaria baicalensis* extract, phellodendron bark extract, barley extract, Dutch mustard extract, seaweed extract, hydrolyzed elastin, hydrolyzed wheat powder, hydrolyzed silk, camomile extract, *Artemisia capillaris* flower extract, licorice extract, Sabdariffa extract, guanosine, Kumazasa (*Sasa albo-marginata*) extract, walnut extract, clematis extract, yeast extract, burdock extract, comfrey extract, bilberry extract, red thorowax root extract, abdominal stalk extract, sage extract, *Saponaria officinalis* extract, Sasa bamboo extract, *Crataegus cuneata* fruit extract, shiitake mushroom extract, rehmannia root extract, Shikon extract, linden extract, Shimotsukeso (*Filipendula multijuga*) extract, sweet flag root extract, birch extract, *Equisetum arvense* extract, *Lonicera japonica* Thunberg extract, *Hedera helix* extract, *Crataegus oxyacantha* extract, *Sambucus nigra* extract, *Achillea millefolium* extract, peppermint extract, mallow extract, *Swertia japonica* extract, jujubi extract, thyme extract, clove extract, *Imperata cylindrica* extract, Citrus unshiu peel extract, Aurantii Amari Cortex extract, *Houttuynia cordata* extract, Natto (fermented soy beans) extract, carrot extract, *Rosa multiflora* extract, hibiscus extract, ophiopogon tuber extract, parsley extract, honey, *Parietaria officinalis* extract, *Isodon japonicus* extract, bisabolol, *Tussilago farfara* extract, *Petasites japonica* Miq. extract, hoelen extract, butcher's bloom extract, propolis, peppermint extract, linden extract, hop extract, pine extract, horse chestnut extract, Lysichitum camtschatcense extract, Sapindus mukurossi extract, peach leaf extract, *Centaurea cyanus* extract, eucalyptus extract, citron extract, mugwort extract, lavender extract, lettuce extract, *Astragalus sinicus* extract, rose extract, rosemary extract, Roman chamomile extract, and royal jelly extract. Other fruit-derived components may be further useful in this regard.

The water-soluble (meth)acrylic polymer is a polymer obtained by polymerizing a (meth)acryloyl group-containing compound having a functional group that exhibits water-solubility (hydrophilic group), and exhibits an adhesive property when the water-soluble (meth)acrylic polymer is contained together with water in the adhesive layer. The water-soluble (meth)acrylic polymer may be a polymer obtained by polymerizing a polyacrylic acid or a neutralized product thereof, a (meth)acrylic acid ester having a hydrophilic group, or a compound having a (meth)acryloyl group such as (meth)acrylic acid amide having a hydrophilic group, for example. In addition, the water-soluble (meth) acrylic polymers may be a homopolymer obtained from a compound having a (meth)acryloyl group of one type or a copolymer obtained from a compound having (meth)acryloyl groups of two types or more.

The hydrophilic group may be, without limitation, any of a cationic hydrophilic group, an anionic hydrophilic group, and a nonionic hydrophilic group.

Examples of the cationic hydrophilic group include, but are not limited to, quaternary ammonium, and examples of the anionic hydrophilic group include, but are not limited to, a carboxy group, a sulfonic group, and a phosphate group, and examples of the nonionic hydrophilic group include, but are not limited to, a hydroxy group and an amino group. The term "(meth)acryloyl group" means an acryloyl group or a methacryloyl group, and the term "(meth)acrylic acid" is defined in the similar manner.

Preferably, the water-soluble (meth)acrylic polymer includes polyacrylic acid. The content of the polyacrylic acid in the adhesive layer is preferably 1 to 5% by mass, more preferably 2 to 6% by mass, in relation to the mass of the entire adhesive layer as the reference. By adjusting the content of the polyacrylic acid to 1% by mass or more, the formability and the shape-retention of the adhesive layer tend to more greatly improve, and by adjusting the content of the polyacrylic acid to 5% by mass or less, the rigidity of the adhesive layer tends not to become high and the adhesion to the skin tends to become higher.

The water-soluble (meth)acrylic polymer may preferably include a neutralized product of polyacrylic acid. The neutralized product of polyacrylic acid may be a completely neutralized product of polyacrylic acid, a partially neutralized product of polyacrylic acid, or a mixture thereof. The term "neutralized product of polyacrylic acid" refers to a salt of a polyacrylic acid, and a sodium salt, a potassium salt, a calcium salt, or an ammonium salt thereof, for example, can be used.

For the neutralized product of polyacrylic acid, the partially neutralized product of polyacrylic acid is preferable because of its high initial adhesion and temporal adhesion. In the neutralized product of polyacrylic acid, in one polymer chain, a structural unit derived from acrylic acid and a structural unit derived from acrylic acid salt are present at an arbitrary ratio. For the partially neutralized product of polyacrylic acid, it is preferable to use a carboxy group in one polymer chain of which 20 to 80 mol % has been neutralized.

The content of the neutralized product of polyacrylic acid in the adhesive layer is preferably 1 to 6% by mass, more preferably 2 to 6% by mass, in relation to the mass of the entire adhesive layer as the reference. By adjusting the content of the neutralized product of polyacrylic acid to 1% by mass or more, an excellent adhesion of the neutralized product of polyacrylic acid can be obtained, and by adjusting the content of the neutralized product of polyacrylic acid to 6% by mass or less, the formability and the shape-retention of the adhesive layer improve. Polyacrylic acid and the neutralized product of polyacrylic acid (preferably the partially neutralized product of polyacrylic acid) may be used in combination, and a suitable content of the respective substance and product when they are used in combination is as described above.

In the (meth)acrylic acid ester having a hydrophilic group, the portion of (meth)acrylic acid ester is preferably an alkyl (meth)acrylic acid ester. The alkyl portion is preferably C1-10 alkyl, and more preferably C1-8 alkyl. In the (meth) acrylic acid ester having a hydrophilic group, the hydrophilic group is preferably present in the alkyl portion.

The adhesive layer contains poly(methyl acrylate/2-ethylhexyl acrylate).

Typically, if the adhesive layer of a conventional gel patch has a light weight, the water content may easily degrade and the adhesion may thus easily degrade. On the other hand, in the present embodiment, when the adhesive layer contains poly(methyl acrylate/2-ethylhexyl acrylate), an excellent adhesion tends to be easily maintained after a long period of time has elapsed even if the mass of the adhesive layer is relatively small.

The poly(methyl acrylate/2-ethylhexyl acrylate) is preferably an aqueous emulsion containing water as a medium. Also, the emulsion of poly(methyl acrylate/2-ethylhexyl acrylate) is preferably an emulsion containing poly(oxyethylene) nonyl phenyl ether as a surfactant or a protective colloid. The residue on evaporation (nonvolatile content) by heating at a temperature higher than the boiling point of the medium (e.g., heating at 105° C. for 3 hours) is preferably 57 to 61%. Examples of such an emulsion include, but are not limited to, Nikasol TS-620 (trade name, a product of Nippon Carbide Industries Co., Inc.). According to the Japanese standards of medical package inserts (2013), when Nikasol TS-620 is evaporated and dried in a water bath and the resultant is dried at 105° C. for 3 hours, the amount of the residue on evaporation is 57 to 61%.

The gel patch of the present embodiment contains water in the adhesive layer. Because the adhesive layer contains water, the skin permeability of the drug improves and its pharmacological action is more effectively exhibited.

The water content is preferably 10 to 90% by mass, more preferably 15 to 88% by mass, and yet more preferably 18 to 85% by mass in relation to the mass of the adhesive layer as the reference.

The surfactant comprises a polyethylene glycol fatty acid ester or a polyoxyethylene sorbitan fatty acid ester. If the physiologically active substance is a fat-soluble substance, by combination of a polyethylene glycol fatty acid ester or a polyoxyethylene sorbitan fatty acid ester therewith, a micelle or an emulsion can be easily formed, and the apparent solubility of the physiologically active substance to the adhesive layer is improved.

Examples of preferable surfactants include, but are not limited to, a monofatty acid ester of polyethylene glycol or a monofatty acid ester of polyoxyethylene sorbitan. The fatty acid constituting the monofatty acid ester described above is preferably a fatty acid having 12 to 18 carbon atoms. Non-limiting examples of the fatty acid having 12 to 18 carbon atoms include lauric acid, myristic acid, pentadecylic acid, palmitic acid, palmitoleic acid, margaric acid, stearic acid, oleic acid, vaccenic acid, linoleic acid, and linolenic acid. In this regard, the fatty acid having 12 to 18 carbon atoms is preferably margaric acid, stearic acid, or oleic acid. A particularly preferable surfactant is monostearic acid polyethylene glycol or polyoxyethylene sorbitan monooleate.

The pH of the adhesive layer is preferably 4.7 to 5.1, and more preferably 4.9 to 5.1. By adjusting the pH to 4.7 or higher, the irritation to the skin decreases, and by adjusting the pH to 5.1 or lower, the formability and the shape-retention of the gel patch can be improved. Particularly, if the base fabric is woven fabric, in particular, if the base fabric is knitted fabric, water may seep from the adhesive layer during forming of the adhesive layer, but if the pH is 4.9 to 5.1, the seeping tends to be suppressed. Note that the pH can be measured in compliance with the pH measurement method by the Japanese Pharmacopoeia general test method and by using a glass composite electrode and diluting a sample with purified water by 20 times, for example.

The mass of the adhesive layer may be 214 to 1000 $g/m^2$, 400 to 1000 $g/m^2$, or 400 to 650 $g/m^2$. By preferably adjusting the mass of the adhesive layer to the range of 400 to 650 $g/m^2$, an excellent feel of fitness can be obtained and the adhesion for a longer time period can be obtained. If the mass of the adhesive layer is adjusted within the above-described range, the thickness of the entire gel patch can be reduced to be thin, thus the gel patch may easily follow the skin, and further, because the step from the peripheral portions may be small when attached, the gel patch tends not to be easily peeled.

To the adhesive layer, other components may be further added, such as a solubilizing agent, a crosslinking agent, a moisturizing agent, a refreshing agent, a stabilizer, an inorganic powder, a coloring agent, a flavoring agent, and a pH adjustor.

The solubilizing agent is added so that the components contained in the adhesive layer would not be precipitated. Examples of the solubilizing agent include, but are not limited to, crotamiton; N-methylpyrrolidone; polyalkylene glycols such as polyethylene glycol (PEG) and polybutylene glycol; polyvinyl alcohols; and fatty acid esters such as isopropyl myristate and diethyl adipate. For the solubilizing agents, one of them can be used alone or two or more of them can be used in combination. The content of the solubilizing agent is preferably 0.1 to 10% by mass in relation to the mass of the adhesive layer as the reference.

The crosslinking agent is added to adjust the crosslinking reaction of the water-soluble (meth)acrylic polymer, and the adhesiveness and conformability of the gel patch to the skin can be adjusted by adjusting the content of the crosslinking agent. For the crosslinking agent, agents that are generally used as a gel patch can be used.

The moisturizing agent is not particularly limited and an agent capable of suppressing evaporation of moisture from the adhesive layer over time can be used. Examples of the moisturizing agent include, but are not limited to, gelatines and polyhydric alcohols such as sorbitol, glycerine, ethyleneglycol, propylene glycol, butanediol, and liquid paraffin. For the moisturizing agents, one of them may be used alone or two or more of them may be used in combination. The content of the moisturizing agent is preferably 3 to 70% by mass in relation to the mass of the adhesive layer as the reference.

The refreshing agent brings about cool and refreshing feeling to the user when the gel patch is used, and the refreshing agent may include aroma. Examples of the refreshing agent include, but are not limited to, thymol, 1-menthol, dl-menthol, 1-isopulegol, and a peppermint oil, and it is preferable to use 1-menthol. The content of the refreshing agent is preferably 0.5 to 3% by mass in relation to the mass of the adhesive layer as the reference.

The stabilizing agent improves the conservation stability of physiologically active substances against light (ultraviolet (UV) light, in particular), heat, or oxygen.

Examples of the stabilizing agent include, but are not limited to, oxybenzone, dibutyl hydroxytoluene (BHT), sodium edetate, UV absorbing agent (e.g., a dibenzoyl methane derivative). The content of the stabilizing agent is preferably 0.01 to 1% by mass in relation to the mass of the adhesive layer as the reference.

The inorganic powder is added to adjust the stickiness obtained when the gel patch is used. Examples of the inorganic powder include, but are not limited to, alumina, light silica, titanium oxide, and synthetic aluminum silicate. The content of the inorganic powder is preferably 0.1 to 10% by mass in relation to the mass of the adhesive layer as the reference.

The gel patch of the present embodiment further comprises a release liner on a surface opposite to the surface of the adhesive layer contacting the base fabric.

The release liner is laminated on the surface opposite to the base fabric from the adhesive layer. Because the release liner is provided, degradation of the water content in the adhesive layer during storage can be prevented and adhesion of dusts to the adhesive layer can be suppressed.

The material of the release liner is not particularly limited and a liner generally used by persons skilled in the art can be used. Examples of the material of the release liner include, but are not limited to, polyethylene, polypropylene, polyethylene terephthalate, and paper, and one of them may be used alone or two or more of them may be used in combination. The material of the release liner is preferably polypropylene or polyethylene terephthalate. In the present subject matter, the release liner can be a base fabric of another gel patch. That is, gel patches can be laminated if one side of the base fabric is made to be a release surface.

The gel patch may be stored in an inside of a pouch. By storing the gel patch inside a pouch, degradation of the water content in the adhesive layer during storage can be prevented and adhesion of dusts to the adhesive layer can be suppressed.

The gel patch of the present embodiment can be produced as follows. First, the physiologically active substance, the water-soluble (meth)acrylic polymer, water, the surfactant, and poly(methyl acrylate/2-ethylhexyl acrylate) are mixed together sufficiently to prepare a paste solution. The obtained paste solution is uniformly extended on the release liner, and the base fabric is laminated thereon to obtain the gel patch. Note that the gel patch may also be produced by extending the paste solution onto the base fabric and then laminating the release liner thereon.

EXAMPLES

Preparation of a Gel Patch

In one exemplary embodiment, as shown in Table 1, the components were sufficiently mixed together to prepare a paste solution. The obtained paste solution was uniformly extended onto the release liner, a base fabric was laminated thereon, and the release liner was peeled off to obtain the gel patches of Examples 1, 2 and Comparative Examples 1 to 3. Note that for the poly(methyl acrylate/2-ethylhexyl acrylate), Nikasol TS-620 (trade name, a product of Nippon Carbide Industries Co., Inc.) was used.

TABLE 1

|  | Example 1 | Example 2 | Comparative Example 1 | Comparative Example 2 | Comparative Example 3 |
|---|---|---|---|---|---|
| l-menthol | 1 | 1 | 1 | 1 | 1 |
| glycol salicylate | 2 | 2 | 2 | 2 | 2 |
| tocopherol acetate | 1 | 1 | 1 | 1 | 1 |
| gelatine | 2.5 | 2.5 | 2.5 | 2.5 | 2.5 |
| partially neutralized product of polyacrylic acid | 3 | 3 | 3 | 3 | 3 |
| polyacrylic acid | 3.5 | 3.5 | 3.5 | 3.5 | 3.5 |
| polyvinyl alcohol | 2.5 | 2.5 | 2.5 | 2.5 | 2.5 |
| Nikasol TS-620 | 8.35 | 8.35 | 0 | 8.35 | 8.35 |
| PEG monostearate | 0.5 | 0 | 0 | 0 | 0 |
| POE hydrogenated castor oil | 0 | 0 | 0 | 0 | 0.5 |
| Polysorbate 80 | 0 | 0.5 | 0 | 0 | 0 |
| crosslinking agent | 0.55 | 0.55 | 0.55 | 0.55 | 0.55 |
| D-sorbitol | 7 | 7 | 7 | 7 | 7 |
| glycerin | 23 | 23 | 23 | 23 | 23 |
| other components | 1.02 | 1.02 | 1.02 | 1.02 | 1.02 |
| purified water | 44.08 | 44.08 | 52.93 | 44.58 | 44.08 |
| total | 100 | 100 | 100 | 100 | 100 |

Evaluation of the Gel Patch of Examples 1 and 2

The obtained gel patch was cut so that the width thereof was 2.5 cm, and the load required for peeling when the gel patch was peeled off at a constant speed of 300 mm/min by using a Tensilon® type tensile testing machine (trade name: RTA-100, a product of A&D Company, Limited).

The results are shown in Table 2. In the gel patch of the Comparative Example 3 containing poly(methyl acrylate/2-ethylhexyl acrylate) in the adhesive layer, the liner peeling force increased in comparison with the gel patch of the Comparative Example 1. On the other hand, in the gel patches of Examples 1 and 2, in which the adhesive layer further contains monostearic acid polyethylene glycol (PEG), or polysorbate 80 in addition to poly(methyl acrylate/2-ethylhexyl acrylate), the liner peeling force was the same as that of the gel patch of the Comparative Example 1.

TABLE 2

|  | Example 1 | Example 2 | Comparative Example 1 | Comparative Example 2 | Comparative Example 3 |
|---|---|---|---|---|---|
| Liner peeling force (N/25 mm) | 0.072 | 0.085 | 0.08 | 0.112 | 0.13 |

Instead of salicylic acid glycol and tocopherol acetate in Example 1, felbinac, ketoprofen, and diclofenac sodium were combined so that the mass thereof was 3% in relation to the mass of the entire adhesive layer to obtain the gel patches of Examples 3 to 5.

The liner peeling force was measured for the gel patches of Examples 3 to 5, and results similar to those of Example 1 were obtained.

Preparation of a Gel Patch

In another exemplary embodiment, as shown in Table 3, the components were thoroughly mixed together to prepare a paste solution. The obtained paste solution was uniformly extended onto the release liner, a base fabric was laminated thereon, and the release liner was peeled off to obtain the gel patches of Example 6 and Comparative Example 4. Note that for the poly(methyl acrylate/2-ethylhexyl acrylate), Nikasol TS-620 (trade name, a product of Nippon Carbide Industries Co., Inc.) was used.

TABLE 3

|  | Example 6 | Comparative Example 4 |
|---|---|---|
| l-menthol | 0.3 | 0.3 |
| gelatine | 2.5 | 2.5 |
| partially neutralized product of polyacrylic acid | 4 | 4 |
| polyvinyl alcohol | 2.5 | 2.5 |
| Nikasol TS-620 | 17 | 0 |
| PEG monostearate | 0.5 | 0.5 |
| crosslinking agent | 1 | 1 |
| glycerin | 33 | 30 |
| other components | 6.2 | 4.2 |
| purified water | 33 | 55 |
| total | 100 | 100 |

Evaluation of the Gel Patch of Example 6

The gel patches of Example 6 and Comparative Example 4 were affixed to the skin of 10 subjects, the temperature of the skin to which the gel patch was affixed was measured over time. The results are shown in Table 4. The temperatures recorded in Table 4 were calculated as an average for 10 subjects. The skin temperature before being affixed and the lowest skin temperature after being affixed were compared for each subject, and the difference was recorded as "body temperature reduction". The value obtained by dividing the "body temperature reduction" by the water content of the gel patch is "body temperature reduction per unit of water".

The effect of the body temperature reduction per unit of water for the gel patch of Example 6 is approximately 1.3 times higher than that for the gel patch of Comparative Example 4, and the gel patch of Example 6 more effectively lowered the skin temperature of the subjects.

TABLE 4

|  | Example 6 | Comparative Example 4 |
| --- | --- | --- |
| Temperature [° C.] (before being affixed) | 34.78 | 34.8 |
| Lowest temperature [° C.] (after being affixed) | 31.49 | 30.57 |
| Body temperature reduction [° C.] | 3.29 | 4.23 |
| Body temperature reduction per unit of water | 0.0997 | 0.0769 |
|  | 1.296 | 1 |

The present subject matter being thus described, it will be apparent that the same may be modified or varied in many ways. Such modifications and variations are not to be regarded as a departure from the spirit and scope of the present subject matter, and all such modifications and variations are intended to be included within the scope of the following claims.

What is claimed is:

1. A gel patch comprising a base fabric, an adhesive layer, and a release liner in this order, wherein
the adhesive layer contains a physiologically active substance, a water-soluble (meth)acrylic polymer, water, a surfactant comprising polyethylene glycol monostearic acid ester, and poly(methyl acrylate/2-ethylhexyl acrylate).

2. The gel patch according to claim 1, wherein the poly(methyl acrylate/2-ethylhexyl acrylate) is obtained from a poly(methyl acrylate/2-ethylhexyl acrylate) emulsion source material.

3. The gel patch according to claim 1, wherein the water-soluble (meth)acrylic polymer comprises polyacrylic acid or a neutralized product of polyacrylic acid.

4. The gel patch according to claim 1, further comprising at least one moisturizing agent selected from gelatin, sorbitol and glycerin.

5. The gel patch according to claim 1, further comprising at least one solubilizing agent comprising polyvinyl alcohol.

* * * * *